United States Patent [19]

Brown et al.

[11] 4,414,849

[45] Nov. 15, 1983

[54] APPARATUS AND A METHOD FOR INDICATING VARIATIONS IN ACOUSTIC PROPERTIES ON AN INTERFACE

[75] Inventors: Michael H. Brown, Didcot; Roger Martin, Faringdon, both of England

[73] Assignee: United Kingdom Atomic Energy Authority, London, England

[21] Appl. No.: 310,867

[22] Filed: Oct. 13, 1981

[30] Foreign Application Priority Data

Oct. 20, 1980 [GB] United Kingdom ............... 8033737

[51] Int. Cl.³ .................... G01F 23/00; G01F 23/28; G01N 29/00
[52] U.S. Cl. .................................. 73/290 V; 73/599
[58] Field of Search ............... 73/290 V, 599, 32 A

[56] References Cited

U.S. PATENT DOCUMENTS

| | | | |
|---|---|---|---|
| 3,427,867 | 2/1969 | Nute et al. | 73/599 |
| 3,603,149 | 9/1971 | McKown | 73/290 V |
| 4,144,517 | 3/1979 | Baumoel | 73/290 V |
| 4,203,324 | 5/1980 | Baumoel | 73/290 V |
| 4,232,544 | 11/1980 | Stapsfield | 73/32 A |
| 4,316,183 | 2/1982 | Palmer et al. | 73/290 V |
| 4,320,659 | 3/1982 | Lynnworth et al. | 73/290 V |

FOREIGN PATENT DOCUMENTS 1300172  6/1962  France .

*Primary Examiner*—Howard A. Birmiel
*Attorney, Agent, or Firm*—William R. Hinds

[57] ABSTRACT

The apparatus provides for detection of variation in acoustic properties at a metal to air interface (18) such as may be caused by arrival of drops of leaking liquid. Ultrasonic signal pulses from transducer (14) are reflected many times back and forth across rod (11) between the transducer and the interface (18). Change in diminution of amplitude with successive reflection can be detected over a multiplicity (e.g. 10) of reflections and indicates change in the acoustic properties of the interface. Comparison is made between a selected early reflected signal pulse and a selected later reflection. Response is inhibited in respect of intermediate reflections.

8 Claims, 7 Drawing Figures

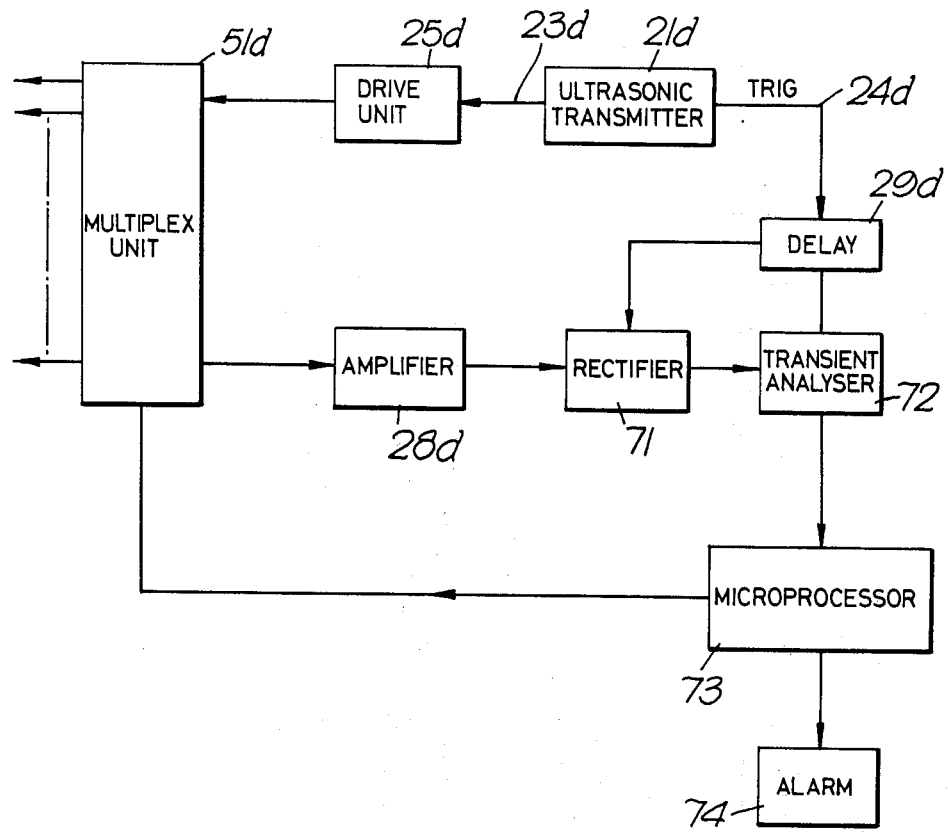

APPARATUS AND A METHOD FOR INDICATING VARIATIONS IN ACOUSTIC PROPERTIES ON AN INTERFACE

BACKGROUND OF THE INVENTION

The invention relates to apparatus for indicating variations in acoustic properties at the interface of a first material in contact with a second material. The apparatus has particular application in the detection of liquid in the form of foam, sludge, wet sand, or droplets on a solid surface such as the inside surface of the wall of a tank or pipe.

Known ultrasonic devices have been used for detecting the presence of substances in tanks or pipelines but require firstly that the substance transmits ultrasound and secondly that sufficient substance is present to fill the path between the transmitter and the receiver.

British Patent Specification No. 1,473,840 discloses a different approach in which changes in the acoustic impedance of material loading an ultrasonic transducer are detected.

Detection of variation in acoustic impedance of a liquid caused by the presence of variable concentrations of gas bubbles is described in British Patent Specification No. 1,474,469. The technique employed in this Specification No. 1,474,469 is to measure the diminution in amplitude of an ultrasonic signal pulse passed through the liquid, the path length being effectively multipled by the use of a reflector to secure repeated traverse by the signal pulse across a relatively short length liquid. This technique is not suitable for detection of foam, sludge, wet sand, or droplets on a solid surface because it is not possible to pass ultrasound through such media.

SUMMARY OF THE INVENTION

The invention is directed to the problem of elimination of spurious results, in particular ensuring that the starting signal amplitude from which each measurement is made is the same and that subsequent spurious signals do not upset the measurement, while avoiding excessive complication in the electronic processing circuits. This problem is met in accordance with the present invention by apparatus for indicating variations in acoustic properties at the interface of a first material in contact with a second material, which first material is capable of transmitting elastic waves therethrough, which apparatus comprises transducer means for injecting an elastic wave signal pulse into the said first material so as to be repeatedly reflected back and forth across the said first material between a surface of predetermined reflection properties and the interface between the first material and the second material, the first material being such that the attenuation with distance of elastic waves traversing therethrough is substantially constant, an amplifier for providing electrical signals corresponding to received reflected signal pulses, detector means for detecting the electrical signal corresponding to an early reflected signal pulse (N), automatic gain control means so controlling the amplifier as to set to a predetermined level the amplitude of the said electrical signal (N) and to determine the gain of the amplifier for subsequent electrical signals corresponding to later reflections of the pulse, comparison means for comparing with a reference standard the amplitude of an electrical signal corresponding to a selected later reflection (N+M) of the pulse, response means for indicating in response to the comparison a change in the attenuation of pulses upon reflection at the said interface, the said response means being inhibited from operating in response to signals corresponding to reflections of the pulse between the said early reflection (N) and the said selected later reflection (N+M).

N and M are chosen to provide a comparison from which changes in signal attenuation upon reflection from the said interface are detectable.

In an example where the first material is a metal forming part of a pipeline and the second material is air in the pipeline which changes to liquid for example when there is liquid leakage into the pipeline, the presence of liquid is detectable when N=4 and M=10.

In another arrangement signal reflections are counted until the signal amplitude diminishes below a predetermined threshold, whereby variations in the count provide an indication of variation in signal attenuation upon reflection from the said interface.

The invention includes apparatus as aforesaid for the detection of arrival presence of foam, sludge, wet sand or liquid droplets upon the surface of a solid.

Preferably the elastic wave signal pulse comprises a short burst of elastic waves at ultrasonic frequency.

BRIEF DESCRIPTION OF THE DRAWINGS

A specific construction of apparatus embodying the invention will now be described by way of example and with reference to the drawings filed herewith, in which:

FIG. 6 is an electrical circuit block diagram of a further modified arrangement.

DETAILED DESCRIPTION OF EMBODIMENTS OF THE INVENTION

The apparatus of this example is intended for detection of arrival presence of liquid on the surface of steel, such as the inside of a steel pipe or tank.

The ratio of reflected to transmitted energy varies in dependence upon the materials forming the interface through which the ultrasonic signal passes. If the interface is steel to air and we assume 100% energy is reflected then when the air is replaced with water only approximately 90% is reflected. This change in reflected energy causes approximately 5% change in the amplitude of a reflected signal, which cannot normally be reliably detected because of its small size and the problem of distinguishing the change from other forms of attenuation and noise in the signal. This problem is overcome in this example by using a metal rod to transmit the ultrasonic signal to the interface. This rod is shaped and dimensioned so that multiple reflected signals are produced and each reflected signal is clearly defined. If the amplitude changes by 5% for each reflection from the steel to water interface then the amplitude of the tenth reflected signal will be $0.95^{10}$ of the amplitude that signal would have if the water were not present.

Figure 2:
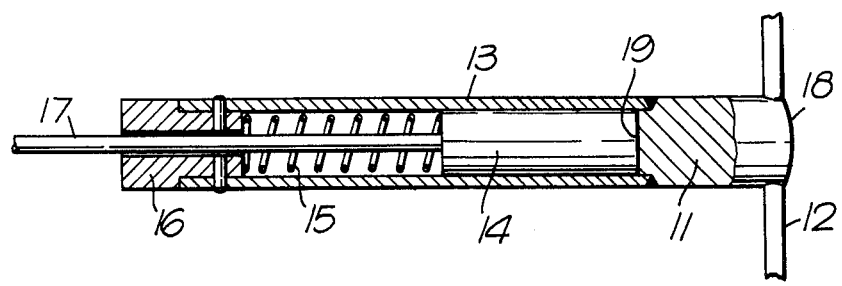
FIG. 2 is a sectional side view of the essential structural components of the apparatus.

Referring to FIG. 2, the cylindrical metal rod 11 forms part of side wall 12 of a metal pipeline. For this the rod 11 is either welded into the wall 12 or formed integrally with a section of the pipeline. A tubular extension 13 welded to the end of the rod 11 remote from the pipe 12 provides a housing for ultrasonic transducer 14. A compression spring 15, clamped in position by a bayonet cap 16 urges the transducer 14 into firm contact with the rod 11. Electrical connection for drive and receive functions of the transducer 14 is provided via lead 17. The surface of the end 18 of the rod 11 forming part of the pipeline wall is formed with a convex curvature to improve the reflection of ultrasonic signals which reverberate back and forth across the rod 11 between the end 18 and the surface 19 in contact with the transducer 14.

The electronic components of the apparatus are arranged to drive the transducer 14 to inject into the rod 11 a brief ultrasonic signal pulse, the reverberations of which are then detected by the transducer 14 in the receive mode. The amplitude of the Nth reflected signal and the (N+M)th reflected signal are compared. Typically N=4 and M=10. It will be appreciated that the signal amplitude is also caused to vary by one or more of the following factors:

(a) changes in the transducer characteristics and its coupling
(b) attenuation in the metal rod, ultrasonic signal scatter and ultrasonic signal divergence.

The factors listed under (b) will normally cause a constant attenuation which will affect the amplitude of the (N+M)th reflected signal but will not cause it to vary under normal operating conditions. The method employed in the apparatus of this example to ovecome the effect of changes in transmission amplitude from factors (a) above is to detect the amplitude of the Nth reflected signal and by feed back control adjust the gain of the amplifier to maintain constant the signal level of this Nth reflected signal. The amplitude of the (N+M)th reflected signal will thus automatically be compensated.

Figure 3:
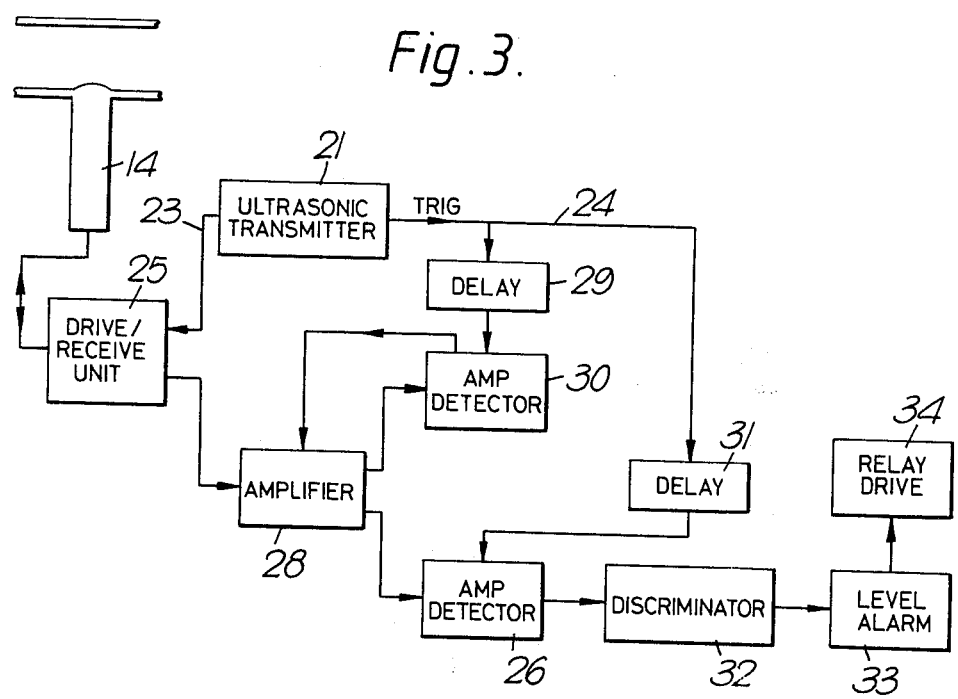
FIG. 3 is an electrical circuit block diagram.

Referring to FIG. 3, an ultrasonic transmitter 21, under control which may be manual but normally would be clock pulsed, provides trigger signals on lines 23, 24. In response to such a trigger signal, a drive/receive unit 25 excites the transducer 14 with a brief pulse at ultrasonic frequency.

Amplifier 28 is protected at its input to withstand the initial transmission signal and is designed to recover quickly from such an overload. A delay 29 is set so as to enable an amplitude detector 30 when the Nth reflected signal is received. Feedback from amplitude detector 30 to the amplifier 28 is based solely upon the detected amplitude of the Nth reflected signal and adjusts the gain of amplifier 28 to give this signal a predetermined fixed amplitude. A further delay 31 is set so as to enable a further amplitude detector 26 when the (N+M)th reflected signal is received. The level of the (N+M)th reflected signal is monitored by discriminator 32 and if the (N+M)th reflected signal amplitude is less than the pre-set discriminator threshold an alarm 33 is triggered. A relay drive 34 is also triggered to provide an automatic control function, if required.

Figure 1A:
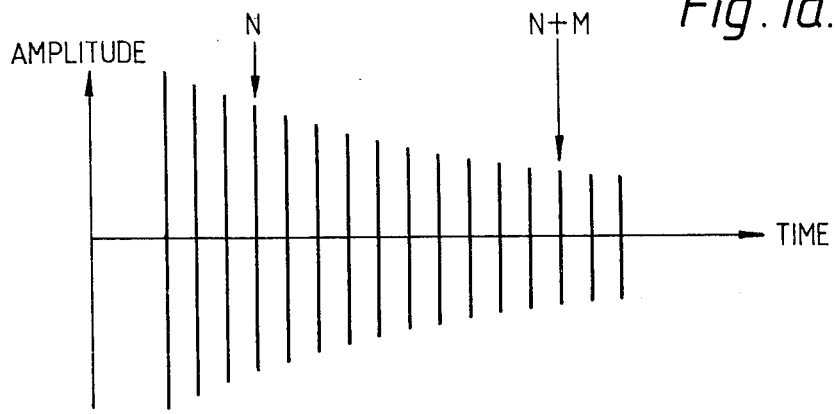
FIG. 1a is a diagrammatic representation of a typical received signal showing successive reflections from a metal to air interface.
Figure 1B:
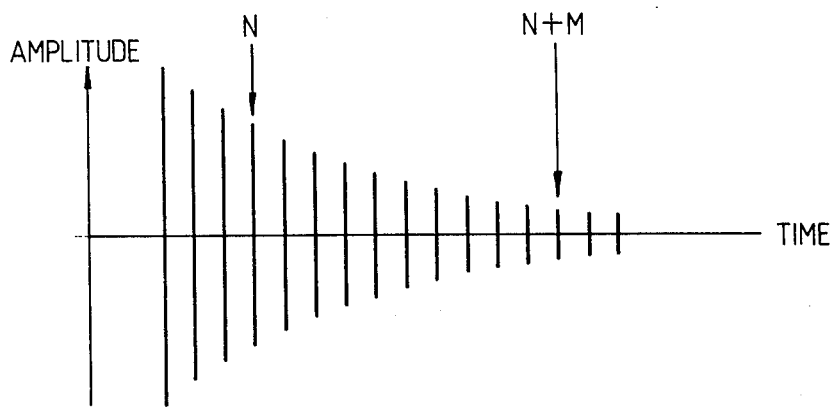
FIG. 1b is a diagrammatic representation of a typical received signal as in FIG. 1a but with water present at the interface.

FIG. 1a shows typical reflected signals for a dry metal to air interface at end 18 of the rod 11. FIG. 1b shows the effect of water droplets on the end 18 of the rod 11. The greater attenuation of the 14th reflected signal (arrowed N+M on the Figures) is immediately apparent. For leak detection, the discriminator 32 is therefore set at the required point just below the "dry" amplitude of the 14th reflected signal such that it will switch on the alarm immediately the amplitude falls to the "wet" amplitude.

Figure 4:
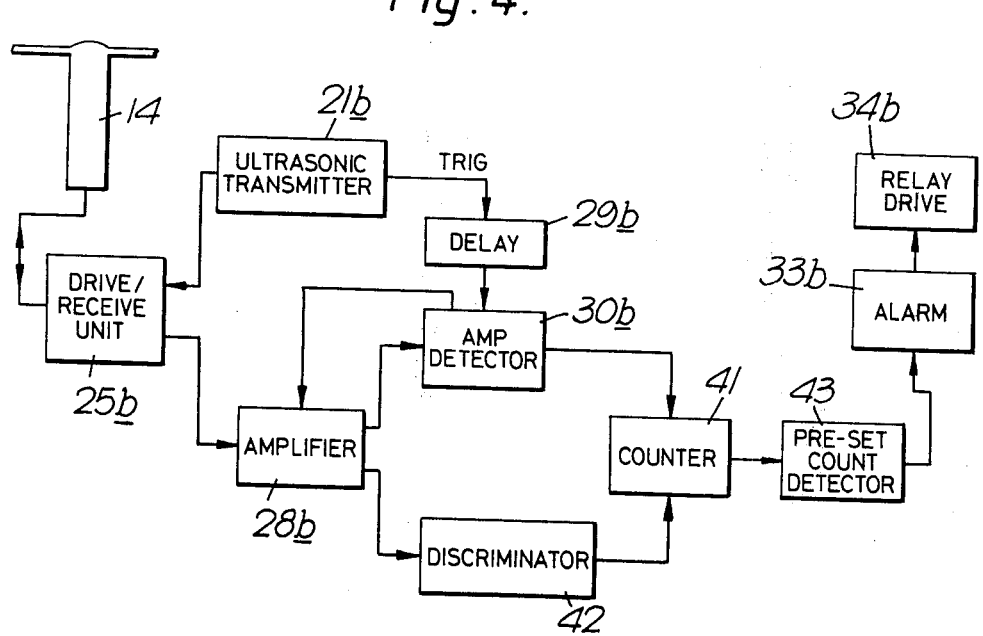
FIG. 4 is an electrical circuit block diagram illustrating a modified arrangement.

FIG. 4 illustrates a modification. Similar components to those described in FIG. 3 are referenced with the same numerals distinguished by a suffix b. Delay 29b and amplitude detector 30b operate in the same way to adjust the gain of amplifier 28b so that the Nth eflected signal always has the same fixed amplitude. The different is that counter 41, started upon receipt of the Nth reflected signal, counts all reflected signals received until stopped by discriminator 42 when the received signal amplitude falls below a predetermined threshold. If the count is less than a predetermined number set in detector 43, alarm 33b is triggered.

Figure 5:
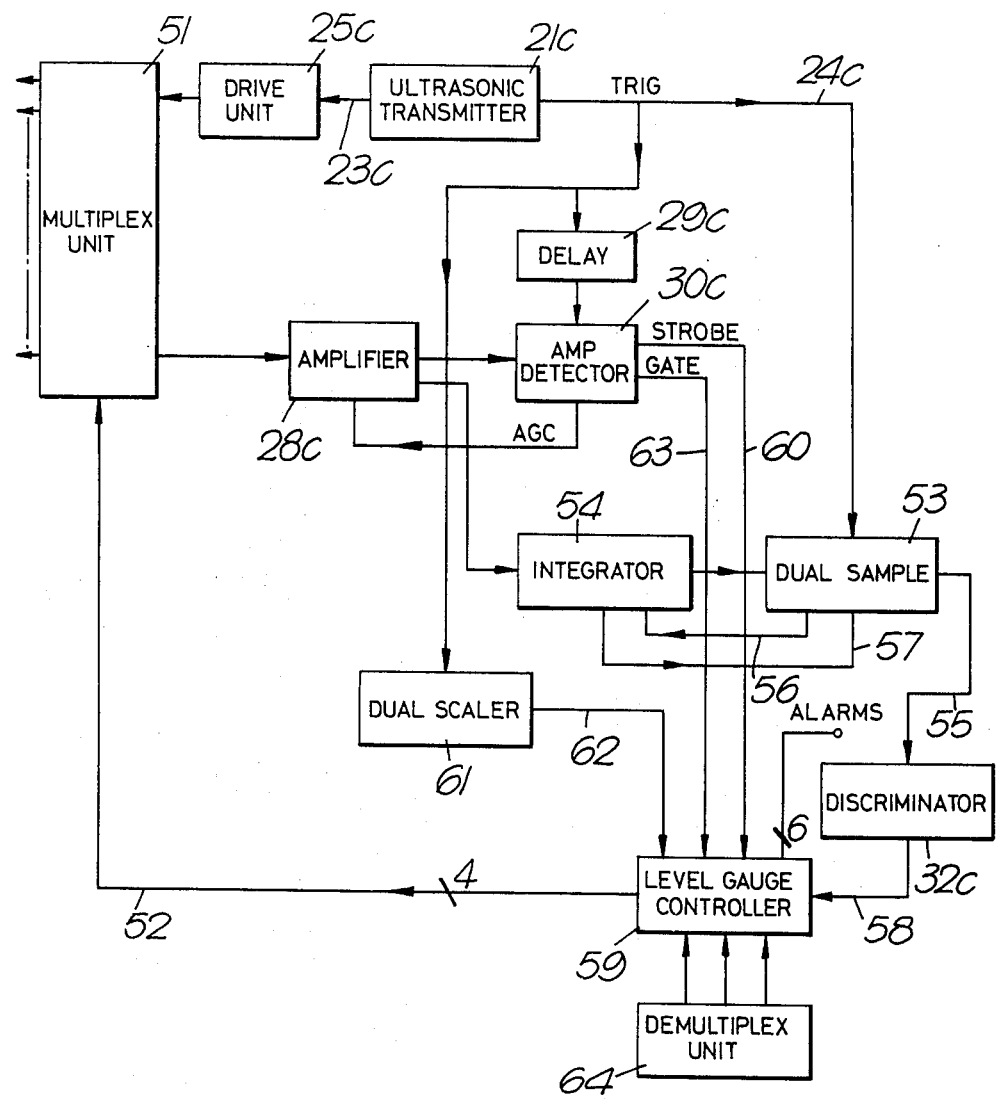
FIG. 5 is an electrical circuit block diagram of another modified arrangement.

FIG. 5 illustrates a further modification in which multiplexing is employed to test sequentially at a plurality of transducers fed from the outputs of multiplex unit 51. The FIG. 5 arrangement also provides for integrating the signal amplitude over several successive reflected signals from (N+M) to (N+M+R) to provide a more reliable determination of the diminution of the signals. It will be appreciated that spurious effects sometimes cause unexpected variation in amplitude of individual reflected signals. If the chosen (N+M)th reflected signal happens to be subject to such a spurious effect, the arrangement of FIG. 3 could give a false alarm.

In FIG. 5 components which perform the same essential function as similar components in FIG. 3 are referenced with the same numerals, distinguished by a suffix c. Ultrasonic transmitter 21c provides trigger pulses on lines 23c and 24c, in response to which all transducers (not shown) receive a drive pulse from drive unit 25c via multiplex unit 51. A 4 bit code signal on line 52 defines the transducer from which received reflected signals are to be passed by the multiplex unit 51 to amplifier 28c. Amplitude detector unit 30c enabled by the trigger signal on line 24c after delay 29c operates in a similar manner to that described in FIG. 3, that is to control the gain of the amplifier 28c to set a fixed level for the Nth reflected signal and to hold the gain constant for successive reflected signals.

Dual sample unit 53 and integrator 54 operate together to provide a signal output on line 55 indicative of the integrated signal amplitude of the (N+M)th to the (N+M+R)th reflected signals. Typically R is 3 or 4.

The dual sample unit 53 interposes a delay following the trigger pulse on line 24c long enough for the (N+M)th reflected signal to be arriving at the amplifier 28c, whereupon a trigger signal from the dual sample unit 53 on line 56 resets the integrator 54. The integrated output over a period encompassing a predetermined number R of reflected signals is sampled by the dual sample unit 53 and a second sample sequence is initiated by a gate signal from the integrator 54 on line 57. In response, the dual sample unit 53 again resets the integrator 54 by a further trigger signal on line 56, the delay being such, in this example, as to ensure that this second sample occurs when reflected signals have died away. The second sample integrated signal output from the integrator 54 is thus representative of random noise. The dual sample unit 53 subtracts the second sample from the first, thus passing on to the discriminator 32c a level indicative of integrated amplitude of R reflected signals from the (N+M)th to the (N+M+R)th reflected signals from which noise level has been subtracted.

If the level is below the pre-set level, thus indicating presence of liquid on the rod to which the transducer is coupled, a signal on line 58 steps on a counter, associated with that transducer, in level gauge controller 59.

The level gauge controller 59 includes a series of such counters, each one associated with one of the transducers. A strobe signal on line 60 derived from amplitude detector 30c defines the correct time interval during which it is appropriate for the discriminator 32c output to be sampled by the level gauge controller 59 and, during this interval, signal samples indicating presence of liquid on a transducer are accumulated in its associated counter and an associated alarm relay is triggered when the count reaches a predetermined level. The system thus requires a plurality of "wet" signal indications to be sampled before the alarm is triggered, thus preventing alarm in response to a spurious single sample.

Dual scaler 61 provides an output on line 62 after a predetermined number of trigger pulses have occurred on line 24c. In this example, output from dual scaler 61 occurs every 100th trigger pulse. In order that the reflected signals from the 100th transmitted ultrasonic pulse are sampled, the level gauge controller 59 does not step on to the next counter and, correspondingly, instruct the multiplex unit 51 to step on to the next transducer until signals are received from both the dual scaler 61 on line 62 and from amplitude detector 30c on line 63. The latter signal, or gating pulse, is timed to occur after the sampling of the reflected signals from the 100th pulse has been completed.

A demultiplex unit 64 is simply a manual overide system allowing particular counter and transducer channels to be selected out of sequence if desired. This is helpful in setting up and maintenance.

FIG. 6 illustrates a further modification. Similar components to those of FIGS. 3 and 5 are again given the same reference numerals distinguished by suffix d. Rectifier 71, in place of amplitude detector 30, simply provides a rectified output of all rflected signals received after the preset delay and this information is digitised in transient analyser 72. The digital representation of the sequence of reflected signals of decaying amplitude is analysed for the rate of decay in microprocessor 73 and compared with standards. Where the comparison indicates "wet" conditions alarm 74 is activated. The microprocessor 73 can, of course, be provided with a range of programmes to meet differing plant conditions and required test facilities.

In the apparatus of this example there are no moving parts and all maintenance (which apart from the electronics can only be the replacing or relocating of the transducer) is easily and quickly performed from outside the tank or pipeline. Such maintenance can quite readily be carried out remotely through radiation shielding if necessary. Provided deposits do not form on the domed end 18 of the rod 11 the apparatus will work in a variety of environments. For example a transducer will be available shortly which will stand high radiation levels. Fairly high temperature liquids can be monitored provided the rod 11 is cooled so that the transducer does not operate above 70° C.

The apparatus of this example can detect the first few drips along the bottom of the pipeline and is therefore particularly suitable as a monitor for liquid leaks through valves, active drain lines, overflow pipelines, or for condensation in steam lines or chemical plants.

The apparatus is also readily adapted for indicating when the level of a foam, liquid, or a wet sludge reaches a predetermined level. Arrival presence of any material can be detected provided it is damp, probably not less than 10% liquid. Possible applications are to control foam levels in chemical reactions, e.g. in breweries, to control sludge levels in settler tanks or to control levels of heavy metal liquors which are often opaque to ultrasound. It is also possible to monitor levels if the apparatus is inserted into the tank and used as a dip stick, which may be motorised or manually operated.

The apparatus may be adapted to indicate approximately the wetness factor of sludges and foams.

The invention is not restricted to the details of the foregoing example. For instance in some applications it is possible to attach a transducer directly onto the outside of a metal or plastics material pipe without introducing a specially prepared rod into the pipe wall. In such a case, however, it is necessary that the pipe wall itself is capable of providing adequately separated reverberating elastic wave signals. Whilst the invention is most likely to find application in pipelines of metal or plastics material, it may be expected to work with any first material which adequately transmits elastic waves, which has a substantially constant characteristic of attenuation with transmission, and which provides an adequate reflection from its surface.

We claim:

1. Apparatus for indicating variations in acoustic properties at the interface of a first material in contact with a second material, which first material is capable of transmitting elastic waves therethrough, which apparatus comprises transducer means for injecting an elastic wave signal pulse into the said first material so as to be repeatedly reflected back and forth across the said first material between a surface of predetermined reflection properties and the interface between the first material and the second material, the first material being such that the attenuation with distance of elastic waves traversing therethrough is substantially constant, an amplifier for providing electrical signals corresponding to received reflected signal pulses, detector means for detecting the electrical signal corresponding to an early reflected signal pulse (N), automatic gain control means so controlling the amplifier as to set to a predetermined level the amplitude of the said electrical signal (N) and to determine the gain of the amplifier for subsequent electrical signals corresponding to later reflections of the pulse, comparison means for comparing with a reference standard the amplitude of an electrical signal corresponding to a selected later reflection (N+M) of the pulse, response means for indicating in response to the comparison a change in the attenuation of pulses upon reflection at the said interface, the said response means being inhibited from operating in response to signals corresponding to reflections of the pulse between the said early reflection (N) and the said selected later reflection (N+M).

2. Apparatus as claimed in claim 1, wherein the first material is a metal forming part of a pipeline and the second material is either air or liquid.

3. Apparatus as claimed in claim 2, wherein the said early reflected signal pulse (N) is selected to be the fourth reflected signal pulse (N=4) and the said later reflection (N+M) is selected to be the fourteenth reflected signal pulse (M=10), whereby change in the second material from air to liquid is detectable.

4. Apparatus as claimed in claim 1, wherein the said comparison means comprises a threshold detector which controls a counter so that the counter counts reflections between the said early reflected signal pulse (N) and a later reflection (N+M) selected by the threshold detector to be the first reflected signal pulse the amplitude of which falls below a predetermined level, and the said response means comprises a present count detector which indicates change in the attenuation of pulses upon reflection at the said interface from the changes in counts accumulated in the counter, the number of counts increasing as the said attenuation decreases and the number of counts decreasing as the said attenuation increases.

5. Apparatus as claimed in claim 1, wherein the said automatic gain control means so control the gain of the amplifier after each injection of an elastic wave signal pulse as to amplify the said predetermined early reflected signal pulse (N) to a predetermined level and hold the gain constant thereafter until the next fresh injection of an elastic wave signal pulse.

6. Apparatus as claimed in claim 1, wherein an integrator integrates the electrical signal corresponding to the said later reflection (N+M) together with the electrical signals corresponding to a number R of subsequent reflections, and the said comparison means compares the integrated amplitude with a reference standard.

7. Apparatus for the detection of arrival presence of foam, sludge, wet sand or liquid droplets upon the surface of a solid which apparatus comprises a transducer for so injecting an elastic wave signal pulse into the said solid that the signal pulse is repeatedly reflected back and forth between the said surface and the transducer, an amplifier for providing electrical signals corresponding to received reflected signal pulses, detector means for detecting the electrical signal corresponding to an early reflected signal pulse (N), automatic gain control means so controlling the amplifier as to set to a predetermined level the amplitude of the said electrical signal (N) and to determine the gain of the amplifier for subsequent electrical signals corresponding to later reflections of the pulse, comparison means for comparing with a reference standard the amplitude of an electrical signal corresponding to a later reflection (N+M) of the pulse, response means for indicating in response to the comparison a change in the attenuation of pulses upon reflection at the said surface, the said response means being inhibited from operating in response to signals corresponding to reflections of the pulse between the said early reflection (N) and the said later reflection (N+M).

8. Apparatus as claimed in claim 7, wherein an integrator integrates the electrical signal corresponding to the said later reflection (N+M) together with the electrical signals corresponding to a number R of subsequent reflections, and the said comparison means compares the integrated amplitude with a reference standard.

* * * * *